(12) United States Patent
Kobayashi (10) Patent No.: US 8,496,833 B2
(45) Date of Patent: Jul. 30, 2013

(54) LEUKOCYTE REMOVAL METHOD

(75) Inventor: Kenji Kobayashi, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 646 days.

(21) Appl. No.: 11/813,329

(22) PCT Filed: Dec. 28, 2005

(86) PCT No.: PCT/JP2005/024035
§ 371 (c)(1),
(2), (4) Date: Oct. 5, 2007

(87) PCT Pub. No.: WO2006/073106
PCT Pub. Date: Jul. 13, 2006

(65) Prior Publication Data
US 2008/0110829 A1    May 15, 2008

(30) Foreign Application Priority Data
Jan. 6, 2005 (JP) ................................. 2005-001830

(51) Int. Cl.
*B01D 11/00* (2006.01)
*B01D 61/00* (2006.01)
*C02F 1/44* (2006.01)

(52) U.S. Cl.
USPC ........... 210/645; 210/335; 210/491; 210/505; 210/782; 210/787; 210/806

(58) Field of Classification Search
USPC ................. 210/645, 335, 491, 505, 782, 787, 210/806
See application file for complete search history.

(56) References Cited

U.S. PATENT DOCUMENTS
4,701,267 A    10/1987 Watanabe et al.
4,925,468 A    5/1990 Kishi et al.
(Continued)

FOREIGN PATENT DOCUMENTS
EP    0 606 646    7/1994
JP    60-193468    10/1985
(Continued)

OTHER PUBLICATIONS
English Language Abstract of JP 60-193468.
(Continued)

*Primary Examiner* — Dirk Bass
(74) *Attorney, Agent, or Firm* — Greenblum & Bernstein, P.L.C.

(57) ABSTRACT

A method of removing leukocytes that through reducing of clogging of a leukocyte removing filter element by blood cell components and plasma proteins being a problem encountered at the time of removing leukocytes from blood, shortens the filtration time at refrigerated filtration and exhibits high leukocyte removing performance at room temperature filtration. There is provided a method of removing leukocytes including filtering blood containing leukocytes through a leukocyte removing filter apparatus having multiple fibrous filter elements with different average fiber diameters to thereby remove leukocytes from the blood, characterized in that use is made of a leukocyte removing filter apparatus wherein the multiple fibrous filter elements include at least leukocyte removing filter element (A) of 2.0 to <4.0 μm average fiber diameter and leukocyte removing filter element (B) of 0.7 to 1.2 μm average fiber diameter and wherein the filter element (B) is disposed downstream of the filter element (A), the leukocyte removing filter element (B) having an average fiber diameter of >17.5% to <50% of that of the filter element (A).

6 Claims, 3 Drawing Sheets

U.S. PATENT DOCUMENTS

| | | | |
|---|---|---|---|
| 5,298,165 | A | 3/1994 | Oka et al. |
| 6,032,807 | A * | 3/2000 | Sternberg et al. ............. 210/491 |
| 6,048,464 | A * | 4/2000 | Tanaka et al. ................ 210/767 |
| 6,267,898 | B1 | 7/2001 | Fukuda et al. |
| 2006/0184085 | A1 | 8/2006 | Kimura et al. |

FOREIGN PATENT DOCUMENTS

| | | |
|---|---|---|
| JP | 1-236064 | 9/1989 |
| JP | 3-173824 | 7/1991 |
| JP | 5-017361 | 1/1993 |
| JP | 07-20872 | 3/1995 |
| JP | 2002-204910 | 7/2002 |
| JP | 2004-215873 | 8/2004 |
| JP | 2004-215875 | 8/2004 |
| WO | 99/00172 | 1/1999 |
| WO | 2004-050146 | 6/2004 |

OTHER PUBLICATIONS

English Language Abstract of JP 1-236064.
English Language Abstract of JP 3-173824.
English Language Abstract of JP 5-017361.
English Language Abstract of JP 2004-215873.
English Language Abstract of JP 2004-215875.
English Language Abstract of JP 2002-204910.
U.S. Appl. No. 11/569,901.
U.S. Appl. No. 11/675,275.
U.S. Appl. No. 10/537,252.
U.S. Appl. No. 10/575,099.
Extended European Search Report issued with respect to European Application No. 05844852.3, dated Feb. 2, 2011.
Japanese Office Action dated Nov. 22, 2011 issued with respect to patent family member Japanese Patent Application No. 2006-550835.

* cited by examiner

LEUKOCYTE REMOVAL METHOD

TECHNICAL FIELD

The present invention relates to a leukocyte removal filter and a leukocyte removal method for removing microaggregates and leukocytes or leukocytes and platelets in blood. More particularly, the present invention relates to a leukocyte removal filter and a leukocyte removal method for removing microaggregates and leukocytes, which may cause blood transfusion reactions, in a whole blood product, an erythrocyte product, a platelet product, a plasma product, and the like used for blood transfusion. In particular, the present invention relates to a leukocyte removal filter and a leukocyte removal method exhibiting excellent filtration performance under both use conditions of an ambient temperature filtration condition and a cold filtration condition.

BACKGROUND ART

In the field of blood transfusion, a leukocyte reduced blood transfusion method, which removes leukocytes in a blood product and transfuses the leukocyte reduced blood product to the recipient, has been widely used in recent years. This is because it was found that relatively slight side effects accompanying blood transfusion, such as headache, nausea, chill, and febrile nonhemolytic reaction, or serious side effects which seriously affect a recipient, such as alloantigen sensitization, viral infection, and post-transfusion graft versus host disease (GVHD), are mainly caused by leukocytes contained in the blood product used for blood transfusion.

It is considered that relatively slight side effects such as headache, nausea, chill, and fever can be prevented by removing leukocytes in the blood product until the leukocyte residual rate becomes $10^{-1}$ to $10^{-2}$ or less. In order to prevent serious side effects such as alloantigen sensitization and viral infection, it is also considered that leukocytes must be removed until the residual rate becomes $10^{-4}$ to $10^{-6}$ or less.

The methods for removing leukocytes in a blood product are roughly classified into two kinds of methods of a centrifugal method in which leukocytes are separated and removed using a centrifuge by utilizing the difference in specific gravity among blood components, and a filtering method in which leukocytes are removed by means of adhesion or adsorption using a filter material comprising fiber mass such as nonwoven fabric, a porous structure having continuous pores or the like. The filtering method which removes leukocytes by means of adhesion or adsorption has advantages such as simple operation and low cost, and is most widely used at present.

The leukocyte removal mechanism by the filter material comprising fiber mass such as nonwoven fabric or a porous structure having continuous pores may be considered that leukocytes contacted with the surface of the filter material adhere to or are adsorbed on the surface of the filter material. As a means for improving the leukocyte removal performance of the conventional filter material, studies have been made to increase the contact frequency of the filter material and leukocytes, that is, to increase the surface area per unit volume of the filter material by reducing the fiber diameter or the pore size of the filter material or increasing the bulk density.

Patent document 1 discloses a leukocyte removal filter using nonwoven fabric having a fiber diameter of less than 3 μm and a bulk density of more than 0.15 g/cm³ to not more than 0.50 g/cm³. Although the above leukocyte removal filter exhibits a certain leukocyte removal performance, an increase in liquid flow resistance and clogging of the filter material tend to occur depending on progress of filtration time, whereby problems, for example an extension of filtration time, suspension of filtration, and inferior blood product recovery occur.

In order to solve the above problems, studies have firstly been made to control the clogging of the filter material due to aggregates in a blood product. Patent document 2 discloses a leukocyte removal filter comprising a set of three types of filter materials in which the product XY of the average fiber diameter X and the average fiber-to-fiber distance Y is specified. This leukocyte removal filter efficiently removes aggregates and leukocytes by indispensably providing a three-layer structure in which a filter material with XY>50 is disposed upstream to capture relatively large microaggregates, a filter material with 50≧XY>7 is disposed downstream of the filter material with XY>50 to capture relatively small microaggregates, and a filter material with 7≧XY is disposed downstream of the filter material with 50≧XY>7.

Patent document 3 discloses a filter in which a filter material which removes gel-like aggregates is disposed upstream of the filter, a filter material which removes microaggregates is disposed downstream of the filter material which removes gel-like aggregates, and a filter material which removes leukocytes is disposed downstream of the filter material which removes microaggregates.

Patent document 4 discloses a filter in which clogging of a filter with microaggregates is controlled by disposing filter materials upstream of the filter that has a lower bulk density than filter materials disposed downstream of the filter.

Though clogging of the filter material due to microaggregates in a blood product can be controlled by using the above technologies, recently an improvement in leukocyte removal performance has been increasingly demanded. Specifically, the leukocyte removal performance of a leukocyte removal rate of 99.99% has been demanded as the standard level. This demand may be dealt with by reducing the fiber diameter of the leukocyte removal filter material layer or the pore diameter of the filter material or increasing the bulk density. As a result, additional new problem that the leukocyte removal filter material layer is clogged with blood cell components (particularly leukocytes and platelets) and plasma proteins (particularly fibrin) occurs. The above technologies are effective for controlling clogging of the prefilter layer caused by aggregates, but are insufficient for suppressing clogging of the leukocyte removal filter material layer caused by blood cell components.

In order to solve this problem, technologies relating to leukocyte removal filter materials combining nonwoven fabrics with different properties have been disclosed. Patent document 5 discloses a filter including a first filter material having an average fiber diameter of 0.3 to 1.6 μm and a second filter material having an average fiber diameter larger than that of the first filter material and disposed upstream of the first filter material. The inventors of the present invention have found that the technology disclosed in the patent document 5 reduces clogging of the first filter material, but does not necessarily solve suspicion of clogging of the second filter material.

Moreover, a change in market environment has posed still another problem. Conventionally, a method has been generally employed in which leukocytes are removed at a hospital bedside from blood subjected to cold storage (stored for six weeks at most) after collection. However, it has become general practice in most Western blood centers to remove leukocytes before storage (prestorage leukocyte reduction) in order to improve the quality of the blood product and manage the leukocyte removal process. As a blood filtration using the prestorage leukocyte reduction, ambient temperature filtration in which blood is filtered at an ambient temperature within one day after collection, and cold filtration in which blood is filtered after storing the blood in a refrigerator for about 1 to 3 days are generally used. While ambient temperature filtration exhibits a reduced filtration time, leakage of leukocytes easily occurs in comparison with blood subjected to cold storage. Cold filtration relatively prevents leakage of leukocytes, although the filtration time is long. Accordingly, a filter used under these conditions is required to achieve a reduction in filtration time in cold filtration and an improvement in leukocyte removal performance in ambient temperature filtration.

A leukocyte removal filter which can be used under ambient temperature filtration conditions and cold filtration conditions has not yet been obtained. Specifically, since the patent document 5 is not aware of such a demand, the leukocyte removal performance may become insufficient in ambient temperature filtration.

Patent document 6 discloses a filter in which the fiber diameter of a second filter material on the blood outlet side is defined in the range of 50% to 90% of the fiber diameter of a first filter material on the blood inlet side. According to the studies conducted by the inventors of the present invention, since the first and second filter materials disclosed in the patent document 6 have fiber diameters close to each other, the difference in the function of the filter materials is deficient, whereby the first and second filter materials cannot be assigned different functions. Therefore, it has been found that the filter can be exhibited only unbalanced performance, i.e. shortened filtration time or high leukocyte removal performance. As a result, only a filter suitable for either cold filtration or ambient temperature filtration can be provided. Specifically, the patent document 6 is not aware of a demand for a filter which achieves both a high leukocyte removal performance in ambient temperature filtration and a reduction in filtration time in cold filtration.

As described above, it has become necessary to achieve both a high leukocyte removal performance in ambient temperature filtration and a reduction in filtration time in cold filtration in view of the new market environment arising from prestorage leukocyte reduction. However, the prior arts are not aware of such a demand. Therefore, a filter exhibiting excellent performance under both ambient temperature filtration conditions and cold filtration conditions has not yet been provided, and a leukocyte removal method using such a leukocyte removal filter has not been known.

[Patent document 1] JP-A-S60-193468
[Patent document 2] JP-A-H01-236064
[Patent document 3] U.S. Pat. No. 4,925,572
[Patent document 4] JP-A-H03-173824
[Patent document 5] JP-A-H05-17361
[Patent document 6] JP-A-2002-204910

DISCLOSURE OF THE INVENTION

Problems to be Solved by the Invention

An object of the present invention is to provide a leukocyte removal method which reduces the filtration time in cold filtration and exhibits high leukocyte removal performance in ambient temperature filtration by reducing clogging of a leukocyte removal filter material with blood cell components and plasma proteins which may cause problems when removing leukocytes in blood.

Means for Solving the Problems

The inventors of the present invention have conducted extensive studies in order to achieve the above object. As a result, the inventors have found a fiber diameter suitable for a fibrous filter material A which can suitably remove leukocytes and plasma proteins and be rarely clogged and a fiber diameter suitable for a filter material B which can efficiently remove leukocytes remaining in the blood from which leukocytes and plasma proteins have been suitably removed. The inventors have also found that a leukocyte removal filter formed by combining the filter material A having a specific fiber diameter with the fibrous filter material B having a specific fiber diameter and disposed downstream of the filter material A achieves both a reduction in filtration time in cold filtration and a high leukocyte removal performance in ambient temperature filtration simultaneously. The inventors have further found that on this occasion the filter materials A and B can be effectively and efficiently assigned different functions by causing the average fiber diameter of the filter material B to appropriately differ from that of the filter material A. The leukocyte removal method according to the present invention has been completed based on the above findings.

Specifically, the present invention provides a leukocyte removal method using a specific leukocyte removal filter given below.

(1) A leukocyte removal method comprising filtering blood containing leukocytes using a leukocyte removal filter including plural fibrous filter materials having different average fiber diameters to remove the leukocytes in the blood, in which the fibrous filter materials including at least a leukocyte removal filter material A having an average fiber diameter of not less than 2.0 µm to less than 4.0 µm and a leukocyte removal filter material B having an average fiber diameter of not less than 0.7 µm to less than 1.2 µm, the filter material B being disposed downstream of the filter material A, and the average fiber diameter of the leukocyte removal filter material B is more than 17.5% to less than 50% of the average fiber diameter of the filter material A.

(2) The leukocyte removal method according to claim 1, wherein the leukocyte removal filter includes a leukocyte removal filter material C having an average fiber diameter of more than 1.2 µm to less than 2.0 µm and disposed between the filter material A and the filter material B.

(3) The leukocyte removal method according to (1) or (2), wherein the leukocyte removal filter includes the filter material A of which the weight in an effective filtration portion is not less than 2% to not more than 40% of the weight of the filter material B.

(4) The leukocyte removal method according to any one of (1) to (3), wherein the leukocyte removal filter further includes a filter material A' formed of the same material as the filter material A and disposed downstream of the filter material B, and the filter materials are symmetrically disposed with respect to a blood inlet side and a blood outlet side.

(5) The leukocyte removal method according to any one of (1) to (4), wherein when a ratio ($t_a/t_c$) of an ambient temperature filtration time ($t_a$) to a cold filtration time ($t_c$) is assumed to be X, and a ratio ($r_a/r_c$) of a leukocyte removal performance ($r_a$) in ambient temperature filtration to a leukocyte removal performance ($r_c$) in cold filtration is assumed to be Y, a geometric mean $(X \times Y)^{0.5}$ of X and Y is not less than 0.5 to not more than 1.

(6) The leukocyte removal method according to (5), wherein the ambient temperature range is 20 to 24° C., and the cold temperature range is 1 to 6° C.

(7) The leukocyte removal method according to any one of (1) to (4), wherein the blood has previously been stored at 1 to 6° C. and is filtered at 1 to 6° C.

(8) The leukocyte removal method according to any one of (1) to (4), wherein the blood has been stored at 20 to 24° C. and is filtered at 20 to 24° C.

Effect of the Invention

According to the leukocyte removal method of the present invention using the specific leukocyte removal filter, insufficient blood recovery due to suspension of filtration can be minimized and the filtration time can be reduced in cold filtration, and a high leukocyte removal performance can be achieved in ambient temperature filtration in comparison with a leukocyte removal method using a leukocyte removal filter based on prior arts. Therefore, the leukocyte removal method according to the present invention is extremely useful as a method of removing leukocytes in blood for a short period of time at a high removal rate under both ambient temperature filtration conditions and cold filtration conditions.

BEST MODE FOR CARRYING OUT THE INVENTION

The present invention is described below in detail.

In the present invention, the term "average fiber diameter" of the leukocyte removal filter refers to a value determined according to the following procedure. Firstly, the filter material is sampled and photographed using a scanning electron microscope. When sampling the filter material, the effective filtration cross-sectional area of the filter material is divided into 0.5 cm-square sections, and six sections are randomly sampled. Three sections among the six sections are sampled from the upstream-side surface, and the remaining three sections are sampled from the downstream-side surface. Each section is observed at a magnification of 2500. The center portion of each section and portions near the center portion are photographed one by one until the total of number of fibers photographed reaches 100 or more. The diameters of all the recognizable fibers in the photograph obtained as above are then measured. The term "diameter" used herein refers to the width of the fiber in the direction perpendicular to the fiber axis. A value obtained by dividing the sum of the diameters of all the measured fibers by the number of the fibers is defined as the average fiber diameter. However, when plural fibers are overlap each other, and a fiber is hidden behind another fiber, whereby the diameter of that fiber cannot be measured, when fibers are melted to form a thick fiber, when fibers with diameter significantly differing from each other are mixed, or the like, the data of such fibers is deleted. If the average fiber diameter significantly differs between the upstream side and the downstream side, such a filter material is not considered to be a single filter material. The term "the average fiber diameter significantly differs" used herein refers to the case where a significant difference is statistically recognized. In this case, the upstream-side filter material and the downstream-side filter material are considered to be different filter materials, and the average fiber diameters of the upstream-side filter material and the downstream-side filter material are separately measured after identifying the interface therebetween.

In the present invention, the average fiber diameter of the filter material A of the leukocyte removal filter is not less than 2.0 μm to less than 4.0 μm, preferably not less than 2.0 μm to less than 3.5 μm, and most preferably not less than 2.0 μm to less than 3.0 μm. The filter material A is required to properly remove blood cell components and plasma proteins and rarely clog. If the average fiber diameter of the filter material A is 4.0 μm or more (similar to that of an ordinary microaggregate removal prefilter), it is difficult to remove blood cell components. If the average fiber diameter of the filter material A is contrary less than 2.0 μm, blood cell components and plasma proteins are removed too much, whereby clogging may improperly be induced. The filter material A may be formed of a plurality of filter materials having different average fiber diameters. In this case, each of the filter materials has an average fiber diameter within the above range.

In the present invention, the average fiber diameter of the filter material B of the leukocyte removal filter is not less than 0.7 μm to not more than 1.2 μm, preferably not less than 0.9 μm to not more than 1.2 μm, and most preferably not less than 1.0 μm to not more than 1.2 μm. Since the filter material B filters the blood from which blood cell components and plasma proteins have been properly removed using the filter material A, the filter material B is required to remove leukocytes or leukocytes and platelets with high efficiency. If the average fiber diameter of the filter material B exceeds 1.2 μm, the removal efficiency of leukocytes or leukocytes and platelets is improperly decreased. Even if the average fiber diameter of the filter material B exceeds 1.2 μm, the removal efficiency can be increased by increasing the filling amount of filter material. However, this measure improperly results in an increase in blood residual loss on the filter material. On the other hand, if the average fiber diameter of the filter material B is less than 0.7 μm, it is difficult to stably produce fabric any more. Moreover, it is unpreferable that the blood flow resistance increases too much, or hemolysis easily occurs in erythrocyte filtration. The filter material B may be formed of plural filter materials having different average fiber diameters. In this case, each of the filter materials has an average fiber diameter within the above range.

In the present invention, the filter materials A and B can be effectively and efficiently assigned different functions by causing the average fiber diameter of the filter material B to appropriately differ from that of the filter material A, whereby both a shortened filtration time in cold filtration and a high leukocyte removal performance in ambient temperature filtration can be more reliably achieved. In order to achieve the above effect, the average fiber diameter of the filter material B is more than 17.5% to less than 50% of that of the filter material A, preferably not less than 30% to not more than 48%, and most preferably not less than 40% to not more than 48%. The average fiber diameter percentage of the filter material B to the filter material A exceeds 17.5% from the ranges of the average fiber diameters of the filter materials A and B described above. If the upper limit of the average fiber diameter percentage is 50% or more contrary, the filter materials A and B cannot be effectively and efficiently assigned different functions due to the small difference in fiber diameters of the filter materials A and B, whereby both a reduced filtration time in cold filtration and a high leukocyte removal performance in ambient temperature filtration cannot unpreferably be achieved simultaneously. When calculating the percentage (%) of the average fiber diameter of the filter material B with respect to the average fiber diameter of the filter material A, if the filter material A is formed of plural filter materials having different average fiber diameters, the filter material having the smallest average fiber diameter is selected, similarly, if the filter material B is formed of plural filter materials having different average fiber diameters, the filter material having the largest average fiber diameter is selected. The percentage of the average fiber diameter of the filter material B with respect to that of the filter material A is thus obtained. Since the filter material A defined in the present invention is disposed upstream of the filter material B, a filter material present downstream of the filter material B does not correspond the filter material A.

It is also effective to insert a filter material C having an intermediate average fiber diameter of the filter materials A and B in between the filter materials A and B. This measure is particularly effective when using a fibrous filter material with a small fiber diameter as the filter material B. Note that the filter material C plays a supplementary role in addition to the filter materials A and B. The average fiber diameter of the filter material C is intermediate length between average fiber diameters of the filter materials A and B. Therefore, the average fiber diameter of the filter material C is preferably more than 1.2 μm and less than 2.0 μm. The filling weight of the filter material C in the effective filtration portion is preferably not more than 100% of the filling weight of the filter material B, more preferably not more than 50%, and most preferably not more than 30%.

In the present invention, the filter materials A, B, and C of the leukocyte removal filter may be individual fiber layers which can be separated each other, or may have a structure in which fiber layers having different average fiber diameters are integrated in a state in which the fiber layers cannot be separated. Each filter material may be formed of plural filter materials having different average fiber diameters insofar as each filter material has an average fiber diameter within the range defined above. For example, the filter material A may be formed of a fibrous filter material $A_1$ having an average fiber diameter of 3.9 μm and a filter material $A_2$ having an average fiber diameter of 2.5 μm. In this case, it is preferable to combine the filter materials so that the average fiber diameter decreases from the upstream side to the downstream side of the leukocyte removal filter.

When combining the filter materials A and B, it is preferable that the filling weight of the filter material A in the effective filtration portion be not less than 2% to not more than 40% of that of the filter material B, more preferably not less than 3% to not more than 30%, and most preferably not less than 4% to not more than 20%. If the value is less than 2% (i.e. the amount of the filter material A is too little or the amount of the filter material B is too much), as a result unpreferably clogging of the filter material B may not be sufficiently prevented, or blood loss may be increased. On the other hand, if the value exceeds 40% (i.e. the amount of the filter material A is too much or the amount of the filter material B is too little), unpreferably blood loss may be increased, or the leukocyte removal performance may become insufficient. When the filter material A is formed of plural filter materials having different average fiber diameters, the total weight of the plural filter materials is taken as the filling weight of the filter material A, likewise, when the filter material B is formed of plural filter materials having different average fiber diameters, the total weight of the filter materials is taken as the weight of the filter material B. The filling weight percentage (%) of the filter material A with respect to the filter material B is thus calculated.

In the present invention, the leukocyte removal filter may include a filter material other than the filter materials A, B, and C. For example, a prefilter for trapping microaggregates may be provided upstream of the filter material A, or a postfilter for ensuring a blood flow path may be provided downstream of the filter material B. Especially in the leukocyte removal filter comprising a flexible housing, it is preferable to dispose the postfilter because the filter material is prevented from adhering to the housing on the blood outlet side. A filter material A' formed of the same material as the filter material A or a filter material C' formed of the same material as the filter material C may be provided downstream of the filter material B. A symmetric structure when viewed from the blood inlet side and the outlet side, such as a structure indicated by A-B-A' or A-C-B-C'-A', may be formed. According to such a symmetric structure, since it is not necessary to identify the inlet side or the outlet side, a possible poor performance due to the wrong filtration direction may be prevented, whereby a filter with high productivity can be realized.

In the present invention, when the ratio $(t_a/t_c)$ of the ambient temperature filtration time $(t_a)$ to the cold filtration time $(t_c)$ using the leukocyte removal filter is assumed to be X and the ratio $(r_a/r_c)$ of the leukocyte removal performance $(r_a)$ in ambient temperature filtration to the leukocyte removal performance $(r_c)$ in cold filtration is assumed to be Y, the geometric mean $(X \times Y)^{0.5}$ of X and Y is preferably not less than 0.5 to not more than 1, more preferably not less than 0.55 to not more than 1, and most preferably not less than 0.6 to not more than 1. The blood flow rate is generally decreased in cold filtration due to high blood viscosity. On the other hand, the blood cell removal performance of the filter tends to increase. Therefore, the cold filtration time $(t_c)$ becomes longer than the ambient temperature filtration time $(t_a)$, and the leukocyte removal performance $(r_c)$ in cold filtration becomes higher than the leukocyte removal performance $(r_a)$ in ambient temperature filtration, whereby X $(=t_a/t_c)$ and Y $(=r_a/r_c)$ tend to become not more than 1. In order for a filter to be applicable under both ambient temperature filtration condition and cold filtration condition, the filter must exhibit a small difference between the performances under both conditions. Specifically, unless the filter is a filter of which both X and Y are close to 1, the filter can be applied to these conditions. If the geometric mean $(X \times Y)^{0.5}$ of X and Y is less than 0.5, there is concern that the cold filtration time expands and/or the leukocyte removal performance in ambient temperature filtration decreases. Furthermore, X and Y have preferable ranges respectively. X is preferably not less than 0.3 to not more than 1, more preferably not less than 0.4 to not more than 1, and most preferably not less than 0.5 to not more than 1. If X is less than 0.3, since the cold filtration time is too longer in comparison with the ambient temperature filtration time, the filtering operation in blood centers and the like may be hindered. Y is preferably not less than 0.55 to not more than 1, more preferably not less than 0.6 to not more than 1, and most preferably not less than 0.65 to not more than 1. If Y is less than 0.55, the leukocyte removal performance in ambient temperature filtration may be insufficient.

The term "cold filtration" used in the present invention refers to a process including storing blood containing leukocytes at 1 to 6° C. and then filtering the blood at 1 to 6° C. The term "ambient temperature filtration" used in the present invention refers to a process including storing blood containing leukocytes at 20 to 24° C. and then filtering the blood at 20 to 24° C.

In the present invention, the filling density of the filter materials A, B, and C in the leukocyte removal filter is preferably not less than 0.1 g/cm$^3$ to not more than 0.4 g/cm$^3$, more preferably not less than 0.13 g/cm$^3$ to not more than 0.3 g/cm$^3$, and most preferably not less than 0.15 g/cm$^3$ to not more than 0.25 g/cm$^3$. If the filling density is less than 0.1 g/cm$^3$, the intermingled portion of the fibers to which leukocytes easily adhere is small. Moreover, there unpreferably occur problems of the handling properties of the filter material and the performance stability in the filter production. If the filling density is 0.4 g/cm$^3$ or more, the filling density of the filter materials is too high and the space serving as a blood flow path is decreased, whereby the filtration flow rate per unit volume of the filter material is significantly decreased. In order to cause blood to uniformly permeate the filter material to reduce a maldistribution of blood flow, the formation index of the filter material corresponding to a thickness of 0.3 mm used as the index indicating the uniformity of the filter material in WO 2004/050146 is preferably not less than 15 to not more than 90, more preferably not less than 15 to not more than 70, and most preferably not less than 15 to not more than 50. If the formation index is 90 or more, there occurs maldistribution of blood flow due to bad uniformity and unevenly distribution of fibers, whereby the leukocyte removal performance per unit volume is decreased. Moreover, the filtration time may be unduly increased because it becomes easy to clog the filter material. On the other hand, if the formation index is less than 15, it is difficult to produce nonwoven fabric, whereby the production efficiency would be unsatisfactory. Therefore, the formation index is preferably 15 or more.

Figure 2:
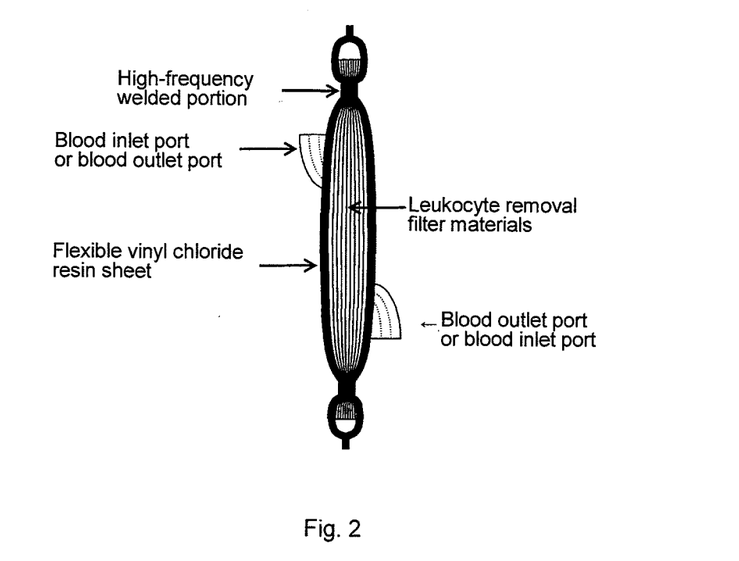
FIG. 2 is a cross-sectional schematic view of a leukocyte removal filter of Example 8 and Comparative Example 7.

The filling density is determined as follows. When using a hard housing, the whole filter materials are compressed to a thickness corresponding to the inner thickness of the hard housing, and the thickness of each filter material is measured from the side surface as it is. When using a flexible housing as shown in FIG. 2, since the filter materials are not compressed, the thickness of the filter material is calculated by multiplying the thickness of each nonwoven fabric by the number of sheets of nonwoven fabric. Regarding to the hard housing or flexible housing, the filling density is calculated by multiplying the calculated thickness by the area of the effective filtration portion to determine the volume of each filter material, and dividing the weight of the filter material by the determined volume.

Each filter material may be preformed to a predetermined thickness and density prior to packing the filter material in the housing of the leukocyte removal filter, or may be integrally preformed into a filter material assembly. As specific examples of the filter material fiber layer used in the present invention, nonwoven fabrics such as melt-blown nonwoven fabric, flash spinning nonwoven fabric, spunbonded nonwoven fabric, spunlaced nonwoven fabric, wet nonwoven fabric, and dry nonwoven fabric and the like, paper, woven fabric, mesh, and the like can be given. As examples of the fiber material, polyamide, polyester, polyacrylonitrile, polyurethane, polyvinyl formal, polyvinyl acetal, polytrifluorochloroethylene, poly(meth)acrylate, polysulfone, polystyrene, polyethylene, polypropylene, cellulose, cellulose acetate, hemp, cotton, silk, glass, carbon, and the like can be given.

In the present invention, the filter material may be subjected to surface modification in order to improve the leukocyte removal performance and optionally the platelet removal performance of the filter material. The filter material may also be subjected to surface modification in order to cause leukocytes to be efficiently adsorbed on the filter material and allow most platelets to pass through the filter material. It is preferable that blood easily permeate the filter material in order to effectively utilize the filter material. Therefore, it is preferable to hydrophilize the surface of the filter material. As a preferred example of the hydrophilic surface, a surface containing a nonionic hydrophilic group and a basic nitrogen-containing functional group can be given. It is more preferable that the hydrophilic surface has a basic nitrogen atom content of not less than 0.2 wt % to not more than 4.0 wt %. As examples of the hydrophilization method for obtaining the hydrophilic surface, a hydrophilic polymer coating, plasma discharge treatment, electron beam irradiation, radiation graft polymerization, and the like can be given.

As the material for the housing of the leukocyte removal filter for containing the filter material, either a hard resin or a flexible resin may be used. As examples of the raw material for the hard resin, phenol resin, acrylic resin, epoxy resin, formaldehyde resin, urea resin, silicon resin, ABS resin, nylon, polyurethane, polycarbonate, polyvinyl chloride, polyethylene, polypropylene, polyester, styrene-butadiene copolymer, and the like can be given. When using the flexible resin, the housing is preferably formed from a sheet-shaped or cylindrical molded product made of a flexible synthetic resin. As preferable examples of the raw material for the flexible resin, thermoplastic elastomers such as soft polyvinyl chloride, polyurethane, ethylene-vinyl acetate copolymer, polyolefins such as polyethylene and polypropylene, hydrogenated styrene-butadiene-styrene copolymer, styrene-isoprene-styrene copolymer or hydrogenated product thereof, and the like, a mixture of the thermoplastic elastomer and a softening agent such as polyolefin or ethylene-ethyl acrylate, and the like can be given. Of these, soft polyvinyl chloride, polyurethane, ethylene-vinyl acetate copolymer, polyolefin, and the thermoplastic elastomer containing these elastomers as the main component are more preferable, with soft polyvinyl chloride and polyolefin being particularly preferable.

The shape of the housing is not particularly limited insofar as the housing has an inlet port for blood before filtration and an outlet port for blood after filtration. The inner surface of the housing may be formed into a concave and convex shape in order to ensure a blood flow path by preventing the housing from closely contacting to the filter material. Particularly when using a flexible housing, the filter material may be pressed against and closely contact to the housing on the blood outlet side by the filtration pressure from the blood inlet side or the negative pressure when recovering the blood after filtration utilizing the elevation head, whereby the blood flow may be hindered. Therefore, it is effective to make the inner surface on the blood outlet-side irregular.

In the present invention, the leukocyte removal filter is obtained as follows. The filter material A and the filter material B are packed in stacked layers so that the filter material A is disposed upstream of the filter material B. The filter materials are sandwiched by a flexible resin sheet(s) having ports serving as a blood inlet port and a blood outlet port, and the end portions of the filter materials and the flexible sheet are integrally welded using a high-frequency welding machine or the like, the leukocyte removal filter can thus be obtained. As described above, plural filter materials may be used in stacked layers as the filter materials A and B, or another filter material may be layered between the filter materials A and B, upstream of the filter material A, or downstream of the filter material B.

The present invention also relates to a leukocyte removal method which includes filtering blood containing leukocytes using the above-described leukocyte removal filter to obtain the blood from which the leukocytes are removed. The method according to the present invention can be used for both ambient temperature filtration and cold filtration. The term "blood" to be filtered according to the present invention generically refers to a liquid comprising whole blood containing leukocytes, or one or more blood components prepared from whole blood, or a liquid prepared by adding an anticoagulant, a preservative solution, and the like thereto. As specific examples of the blood, a whole blood product, an erythrocyte product, a platelet product, a plasma product, a washed erythrocyte suspension, a frozen thawed concentrated red cells, a synthetic blood, a platelet rich plasma, a buffy coat, and the like can be given. Note that the blood is not limited thereto. In particular, use of the leukocyte removal filter according to the present invention is useful when filtering a whole blood product containing a large number of leukocytes or an erythrocyte product which requires a relatively long filtration time due to high viscosity.

EXAMPLES

The present invention is described below in more detail by way of examples. Note that the present invention is not limited to the following examples.

Example 1

A nonwoven fabric $A_1$ formed of polyethylene terephthalate (hereinafter abbreviated as "PET") and having an average fiber diameter of 3.9 µm, a weight per unit area (Metsuke) (weight of the filter material per unit filtration area) of 60 g/m² and a specific surface area of 0.7 m²/g was used as the filter material A, and a PET nonwoven fabric $B_1$ having an average fiber diameter of 1.2 µm, a weight per unit area of 40 g/m² and a specific surface area of 1.5 m²/g was used as the filter material B. The specific surface area of each filter material was determined by measuring the surface area of 0.3 g of the filter material using a specific surface area meter (SHIMADZU Micromeritics TriStar). A column having an effective filtration area of 1.33 cm² was packed with the filter material $A_1$ having a filling weight in the effective filtration portion of 8.0 mg (weight of the filter material hereinafter refers to the filling weight in the effective filtration portion) and the filter material $B_1$ having a filling weight in the effective filtration portion of 58.5 mg in layers so that the filter material $A_1$ was disposed upstream of the filter material $B_1$. The average fiber diameter of the filter material $B_1$ was 30.8% of the average fiber diameter of the filter material $A_1$, and the filling weight of the filter material $A_1$ in the effective filtration portion was 13.6% of the weight of the filter material $B_1$.

Figure 1:
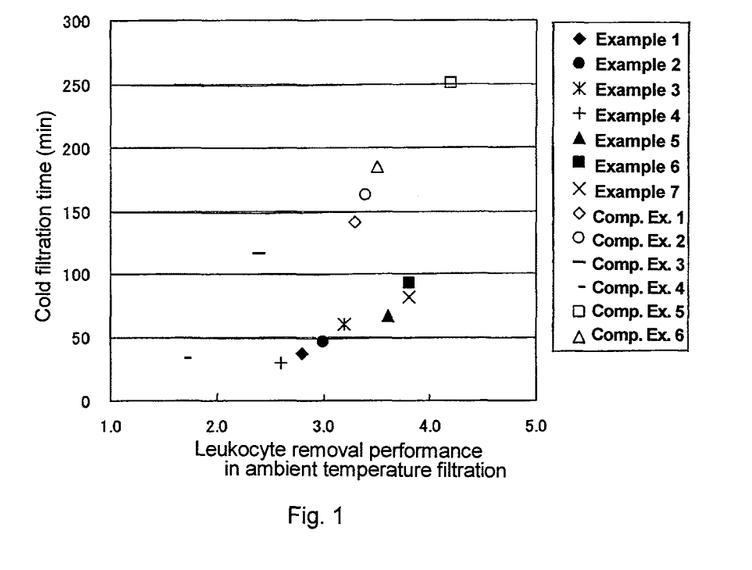
FIG. 1 is a graph showing the relationship between the leukocyte removal performance in ambient temperature filtration and the cold filtration time in Examples 1 to 7 and Comparative Examples 1 to 6.

The filtration performance was evaluated according to the following method. The filtration time and the leukocyte removal performance in ambient temperature filtration were respectively 24.0 minutes and 2.8, and the filtration time and the leukocyte removal performance in cold filtration were respectively 37.2 minutes and 4.1. The specifications of the filter materials and the filtration performance evaluation results of the filters of Examples 1 to 7 and Comparative Examples 1 to 6 are summarized in Table 1 and FIG. 1.

(Filtration Performance Evaluation)

An erythrocyte product prepared as follows was used for filtration performance evaluation. 450 mL of whole blood was collected and mixed into a blood bag containing 63 mL of an anticoagulant CPD. After centrifugation, supernatant plasma was removed. 100 mL of red blood cell preservative solution AS-1 were added to the remaining concentrated red blood cells to prepare an erythrocyte product on the day the blood was collected. The resulting erythrocyte product was filtered through the column under the two conditions of ambient temperature filtration condition and cold filtration condition. In ambient temperature filtration, the erythrocyte product was filtered after storing at the ambient temperature until the next day of the blood collection. In cold filtration, the erythrocyte product was stored in a refrigerator at 4° C. and filtered at 4° C. after three days from collection. In both ambient temperature filtration and cold filtration, the erythrocyte product was filtered at elevation head of 50 cm. Filtration was terminated when 4 mL of the filtrate was collected. The filtration time from the start to termination of filtration was measured. The leukocyte removal performance was calculated according to the following equation (1).

Leukocyte removal performance=Log (leukocyte concentration before filtration (number/µL)/leukocyte concentration after filtration (number/4))  (1)

The leukocyte concentration before filtration was measured using an automated hematology analyzer SF3000 (manufactured by Sysmex Corporation), and the leukocyte concentration after filtration was measured by a flow cytometry method using a LeucoCOUNT kit and an FACSCALIBUR (manufactured by Becton, Dickinson and Company).

Example 2

A PET nonwoven fabric $A_2$ having an average fiber diameter of 2.5 µm, a weight per unit area of 60 g/m² and a specific surface area of 0.8 m²/g was used as the filter material A, and the PET nonwoven fabric $B_1$ having an average fiber diameter of 1.2 µm, a weight per unit area of 40 g/m² and a specific surface area of 1.5 m²/g was used as the filter material B. The column described above was packed with 8.0 mg of the filter material $A_2$ and 58.5 mg of the filter material $B_1$ in layers so that the filter material $A_2$ was disposed upstream of the filter material $B_1$. The average fiber diameter of the filter material $B_1$ was 48.0% of the average fiber diameter of the filter material $A_1$, and the weight of the filter material $A_2$ in the effective filtration portion was 13.6% of the weight of the filter material $B_1$. The filtration performance of the filter was evaluated in the same manner as in Example 1. The filtration time and the leukocyte removal performance in ambient temperature filtration were respectively 27.6 minutes and 3.0, and the filtration time and the leukocyte removal performance in cold filtration were respectively 46.8 minutes and 4.0.

Example 3

A PET nonwoven fabric $A_3$ having an average fiber diameter of 2.1 µm, a weight per unit area of 60 g/m² and a specific surface area of 0.9 m²/g was used as the filter material A, and a PET nonwoven fabric $B_2$ having an average fiber diameter of 1.0 µm, a weight per unit area of 40 g/m² and a specific surface area of 1.8 m²/g was used as the filter material B. The column described above was packed with 8.0 mg of the filter material $A_3$ and 58.5 mg of the filter material $B_2$ in layers so that the filter material $A_3$ was disposed upstream of the filter material $B_2$. The average fiber diameter of the filter material $B_2$ was 47.6% of the average fiber diameter of the filter material $A_3$, and the weight of the filter material $A_3$ in the effective filtration portion was 13.6% of the weight of the filter material $B_2$. The filtration performance of the filter was evaluated in the same manner as in Example 1. The filtration time and the leukocyte removal performance in ambient temperature filtration were respectively 30.8 minutes and 3.2, and the filtration time and the leukocyte removal performance in cold filtration were respectively 60.0 minutes and 4.4.

Example 4

The PET nonwoven fabric $A_2$ having an average fiber diameter of 2.5 μm, a weight per unit area of 60 g/m$^2$ and a specific surface area of 0.8 m$^2$/g was used as the filter material A, a PET nonwoven fabric $C_1$ having an average fiber diameter of 1.8 μm, a weight per unit area of 60 g/m$^2$ and a specific surface area of 1.1 m$^2$/g was used as the filter material C, and the PET nonwoven fabric $B_1$ having an average fiber diameter of 1.2 μm, a weight per unit area of 40 g/m$^2$ and a specific surface area of 1.5 m$^2$/g was used as the filter material B. The column described above was packed with 16.0 mg of the filter material $A_2$, 8.0 mg of the filter material $C_1$ and 42.6 mg of the filter material $B_1$ in layers so that the filter materials $A_2$, $C_1$, and $B_1$ were disposed in that order from the upstream side. The average fiber diameter of the filter material $B_1$ was 48.0% of the average fiber diameter of the filter material $A_2$, and the weight of the filter material $A_2$ in the effective filtration portion was 37.5% of the weight of the filter material $B_1$. The filtration performance of the filter was evaluated in the same manner as in Example 1. The filtration time and the leukocyte removal performance in ambient temperature filtration were respectively 18.2 minutes and 2.6, and the filtration time and the leukocyte removal performance in cold filtration were respectively 29.6 minutes and 3.5.

Example 5

A PET nonwoven fabric $A_4$ having an average fiber diameter of 3.0 μm, a weight per unit area of 60 g/m$^2$ and a specific surface area of 0.75 m$^2$/g was used as the filter material A, and a PET nonwoven fabric $B_3$ having an average fiber diameter of 0.9 μm, a weight per unit area of 40 g/m$^2$ and a specific surface area of 2.0 m$^2$/g was used as the filter material B. The column described above was packed with 8.0 mg of the filter material $A_4$ and 58.5 mg of the filter material $B_3$ in layers so that the filter material $A_4$ was disposed upstream of the filter material $B_3$. The average fiber diameter of the filter material $B_3$ was 30.0% of the average fiber diameter of the filter material $A_4$, and the weight of the filter material $A_4$ in the effective filtration portion was 13.6% of the weight of the filter material $B_3$. The filtration performance of the filter was evaluated in the same manner as in Example 1. The filtration time and the leukocyte removal performance in ambient temperature filtration were respectively 33.5 minutes and 3.6, and the filtration time and the leukocyte removal performance in cold filtration were respectively 67.3 minutes and 4.7.

Example 6

The PET nonwoven fabric $A_4$ having an average fiber diameter of 3.0 μm, a weight per unit area of 60 g/m$^2$ and a specific surface area of 0.75 m$^2$/g was used as the filter material A, and a PET nonwoven fabric $B_4$ having an average fiber diameter of 0.7 μm, a weight per unit area of 40 g/m$^2$ and a specific surface area of 2.5 m$^2$/g was used as the filter material B. The column described above was packed with 8.0 mg of the filter material $A_4$ and 58.5 mg of the filter material $B_4$ in layers so that the filter material $A_4$ was disposed upstream of the filter material $B_4$. The average fiber diameter of the filter material $B_4$ was 23.3% of the average fiber diameter of the filter material $A_4$, and the weight of the filter material $A_4$ in the effective filtration portion was 13.6% of the weight of the filter material $B_4$. The filtration performance of the filter was evaluated in the same manner as in Example 1. The filtration time and the leukocyte removal performance in ambient temperature filtration were respectively 40.9 minutes and 3.8, and the filtration time and the leukocyte removal performance in cold filtration were respectively 93.0 minutes and 4.8.

Example 7

The PET nonwoven fabric $A_1$ having an average fiber diameter of 3.9 μm, a weight per unit area of 60 g/m$^2$ and a specific surface area of 0.7 m$^2$/g was used as the filter material A, and the PET nonwoven fabric $B_4$ having an average fiber diameter of 0.7 μm, a weight per unit area of 40 g/m$^2$ and a specific surface area of 2.5 m$^2$/g was used as the filter material B. The column described above was packed with 8.0 mg of the filter material $A_1$ and 58.5 mg of the filter material $B_4$ in layers so that the filter material $A_1$ was disposed upstream of the filter material $B_4$. The average fiber diameter of the filter material $B_4$ was 17.9% of the average fiber diameter of the filter material $A_1$, and the weight of the filter material $A_1$ in the effective filtration portion was 13.6% of the weight of the filter material $B_4$. The filtration performance of the filter was evaluated in the same manner as in Example 1. The filtration time and the leukocyte removal performance in ambient temperature filtration were respectively 38.8 minutes and 3.8, and the filtration time and the leukocyte removal performance in cold filtration were respectively 81.3 minutes and 4.7.

Comparative Example 1

A PET nonwoven fabric $P_1$ having an average fiber diameter of 12 μm, a weight per unit area of 30 g/m$^2$ and a specific surface area of 0.24 m$^2$/g was used as a prefilter, and the PET nonwoven fabric $B_1$ having an average fiber diameter of 1.2 μm, a weight per unit area of 40 g/m$^2$ and a specific surface area of 1.5 m$^2$/g was used as the filter material B. The column described above was packed with 8.0 mg of the prefilter $P_1$ and 58.5 mg of the filter material $B_1$ in layers so that the prefilter $P_1$ was disposed upstream of the filter material $B_1$. The filtration performance of the filter was evaluated in the same manner as in Example 1. The filtration time and the leukocyte removal performance in ambient temperature filtration were respectively 32.4 minutes and 3.3, and the filtration time and the leukocyte removal performance in cold filtration were respectively 141.5 minutes and 4.5.

Comparative Example 2

The PET nonwoven fabric $C_1$ having an average fiber diameter of 1.8 μm, a weight per unit area of 60 g/m$^2$ and a specific surface area of 1.1 m$^2$/g was used as the filter material C, and the PET nonwoven fabric $B_1$ having an average fiber diameter of 1.2 μm, a weight per unit area of 40 g/m$^2$ and a specific surface area of 1.5 m$^2$/g was used as the filter material B. The column described above was packed with 8.0 mg of the filter material $C_1$ and 58.5 mg of the filter material $B_1$ in layers so that the filter material $C_1$ was disposed upstream of the filter material $B_1$. The filtration performance of the filter was evaluated in the same manner as in Example 1. The filtration time and the leukocyte removal performance in ambient temperature filtration were respectively 33.6 minutes and 3.4, and the filtration time and the leukocyte removal performance in cold filtration were respectively 162.8 minutes and 4.5.

Comparative Example 3

The PET nonwoven fabric $C_1$ having an average fiber diameter of 1.8 μm, a weight per unit area of 60 g/m$^2$ and a specific surface area of 1.1 m$^2$/g was used as the filter material C, and a PET nonwoven fabric $C_2$ having an average fiber diameter of 1.4 μm, a weight per unit area of 40 g/m$^2$ and a specific surface area of 1.3 m$^2$/g was used as another filter material C. The column described above was packed with 8.0 mg of the filter material $C_1$ and 58.5 mg of the filter material $C_2$ in layers so that the filter material $C_1$ was disposed upstream of the filter material $C_2$. The filtration performance of the filter was evaluated in the same manner as in Example 1. The filtration time and the leukocyte removal performance in ambient temperature filtration were respectively 29.3 minutes and 2.4, and the filtration time and the leukocyte removal performance in cold filtration were respectively 116.3 minutes and 3.4.

Comparative Example 4

The PET nonwoven fabric $A_2$ having an average fiber diameter of 2.5 μm, a weight per unit area of 60 g/m$^2$ and a specific surface area of 0.8 m$^2$/g was used as the filter material A, and the PET nonwoven fabric $C_2$ having an average fiber diameter of 1.4 μm, a weight per unit area of 40 g/m$^2$ and a specific surface area of 1.3 m$^2$/g was used as the filter material C. The column described above was packed with 8.0 mg of the filter material $A_2$ and 58.5 mg of the filter material $C_2$ in layers so that the filter material $A_2$ was disposed upstream of the filter material $C_2$. The filtration performance of the filter was evaluated in the same manner as in Example 1. The filtration time and the leukocyte removal performance in ambient temperature filtration were respectively 13.7 minutes and 1.7, and the filtration time and the leukocyte removal performance in cold filtration were respectively 33.9 minutes and 3.3.

Comparative Example 5

A PET nonwoven fabric $A_4$ having an average fiber diameter of 3.0 μm, a weight per unit area of 60 g/m$^2$ and a specific surface area of 0.75 m$^2$/g was used as the filter material A, and a PET nonwoven fabric having an average fiber diameter of 0.5 μm, a weight per unit area of 40 g/m$^2$ and a specific surface area of 3.4 m$^2$/g was used as a filter material D. The column described above was packed with 8.0 mg of the filter material $A_4$ and 58.5 mg of the filter material D in layers so that the filter material $A_4$ was disposed upstream of the filter material D. The filtration performance of the filter was evaluated in the same manner as in Example 1. The filtration time and the leukocyte removal performance in ambient temperature filtration were respectively 56.4 minutes and 4.2, and the filtration time and the leukocyte removal performance in cold filtration were respectively 250.5 minutes and 5.0.

Comparative Example 6

A PET nonwoven fabric $P_2$ having an average fiber diameter of 4.1 μm, a weight per unit area of 60 g/m$^2$ and a specific surface area of 0.65 m$^2$/g was used as a prefilter, and the PET nonwoven fabric $B_3$ having an average fiber diameter of 0.9 μm, a weight per unit area of 40 g/m$^2$ and a specific surface area of 2.0 m$^2$/g was used as the filter material B. The column described above was packed with 8.0 mg of the prefilter $P_2$ and 58.5 mg of the filter material $B_3$ in layers so that the prefilter $P_2$ was disposed upstream of the filter material $B_3$. The filtration performance of the filter was evaluated in the same manner as in Example 1. The filtration time and the leukocyte removal performance in ambient temperature filtration were respectively 47.3 minutes and 3.5, and the filtration time and the leukocyte removal performance in cold filtration were respectively 184.7 minutes and 4.5.

Example 8

The PET nonwoven fabric $P_1$ having an average fiber diameter of 12 μm, a weight per unit area of 30 g/m$^2$ and a specific surface area of 0.24 m$^2$/g was used as a prefilter. The PET nonwoven fabric $A_2$ having an average fiber diameter of 2.5 μm, a weight per unit area of 60 g/m$^2$ and a specific surface area of 0.8 m$^2$/g was used as the filter material A. The PET nonwoven fabric $C_1$ having an average fiber diameter of 1.8 μm, a weight per unit area of 60 g/m$^2$ and a specific surface area of 1.1 m$^2$/g was used as the filter material C. The PET nonwoven fabric $B_3$ having an average fiber diameter of 1.1 μm, a weight per unit area of 40 g/m$^2$ and a specific surface area of 1.6 m$^2$/g was used as the filter material B. The filter materials were layered in the order of $P_1$-$A_2$-$C_1$-$B_3$ from the upstream side. A filter material $C_1$' formed of the same material as the filter material $C_1$, a filter material $A_2$' formed of the same material as the filter material $A_2$ and a filter material $P_1$' formed of the same material as the filter material $P_1$ were further layered toward the downstream side to prepare a filter material having a symmetric structure ($P_1$-$A_2$-$C_1$-$B_3$-$C_1$'-$A_2$'-$P_1$') as a whole. The filter material was sandwiched by a flexible vinyl chloride resin sheet(s) having a port(s) for a blood inlet or a blood outlet, and the end portions of the filter material and the flexible sheet were integrally welded using a high-frequency welding machine to prepare a leukocyte removal filter with an effective filtration area of 56 cm$^2$ having a cross-sectional structure shown in FIG. 2. The average fiber diameter of the filter material $B_3$ was 44.0% of the average fiber diameter of the filter material $A_2$, and the weight of the filter material $A_2$ in the effective filtration portion was 6.8% of the weight of the filter material $B_3$. The filtration performance was evaluated according to the following method. The filtration time and the leukocyte removal performance in ambient temperature filtration were respectively 13 minutes and 4.0, and the filtration time and the leukocyte removal performance in cold filtration were respectively 25 minutes and 4.5. The details and the filtration performance evaluation results of the filters of Example 8 and Comparative Example 7 are summarized in Table 2.

(Filtration Performance Evaluation)

An erythrocyte product prepared as follows was used for filtration performance evaluation. 450 mL of whole blood was collected and mixed into a blood bag containing 63 mL of an anticoagulant CPD. After centrifugation, supernatant plasma was removed. 100 mL of red blood cell preservative solution AS-1 were added to the remaining concentrated red blood cells to prepare an erythrocyte product on the day the blood was collected. The resulting erythrocyte product was filtered through the above filter under two conditions of ambient temperature filtration condition and cold filtration condition. In ambient temperature filtration, the erythrocyte product was filtered at an ambient temperature on the day the erythrocyte product was prepared. In cold filtration, the erythrocyte product was stored in a refrigerator at 4° C. and filtered at 4° C. after three days from the collection. In both ambient temperature filtration and cold filtration, the erythrocyte product was filtered at elevation head of 110 cm. Filtration was terminated when 300 mL of the filtrate was collected. The filtration time from the start to termination of filtration was measured. The leukocyte removal performance was evaluated in the same manner as in Example 1.

Comparative Example 7

The PET nonwoven fabric $P_1$ having an average fiber diameter of 12 μm, a weight per unit area of 30 g/m² and a specific surface area of 0.24 m²/g was used as a prefilter, the PET nonwoven fabric $C_1$ having an average fiber diameter of 1.8 μm, a weight per unit area of 60 g/m² and a specific surface area of 1.1 m²/g was used as the filter material C, and the PET nonwoven fabric $B_3$ having an average fiber diameter of 1.1 μm, a weight per unit area of 40 g/m² and a specific surface area of 1.6 m²/g was used as the filter material B. The filter materials were layered in the order of $P_1$-$C_1$-$B_3$ from the upstream side. A filter material $C_1'$ formed of the same material as the filter material $C_1$ and a filter material $P_1'$ formed of the same material as the filter material $P_1$ were further layered toward the downstream side to prepare a filter material having a symmetric structure indicated by $P_1$-$C_1$-$B_3$-$C_1'$-$P_1'$ as a whole. A leukocyte removal filter similar to that of Example 5 was prepared using the resulting filter material. The filtration performance of the filter was evaluated in the same manner as in Example 7. The filtration time and the leukocyte removal performance in ambient temperature filtration were respectively 16 minutes and 4.2. However, the filtration time in cold filtration was significantly extended to 78 minutes. The leukocyte removal performance in cold filtration was 4.5.

Figure 3:
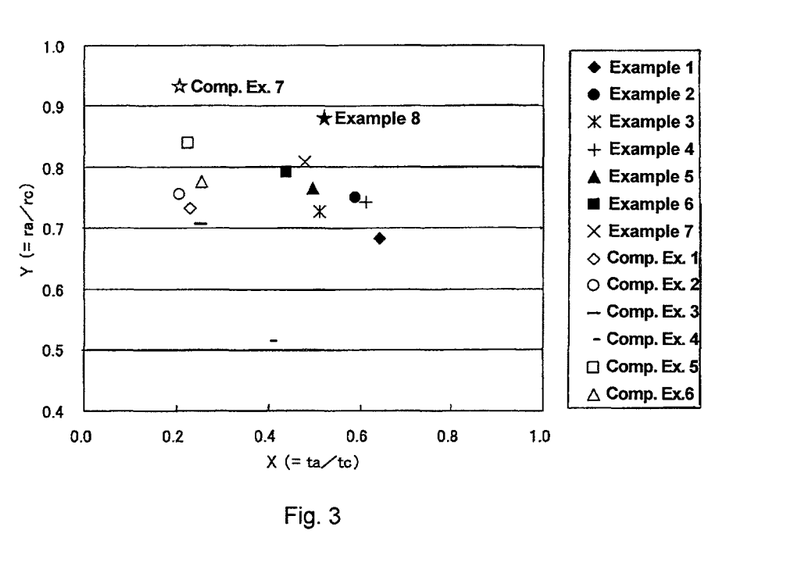
FIG. 3 is a graph showing the relationship between X (=ambient temperature filtration time $t_a$/cold filtration time $t_c$) and Y (=leukocyte removal performance in ambient temperature filtration $r_a$/leukocyte removal performance in cold filtration $r_c$) in Examples 1 to 8 and Comparative Examples 1 to 7.
Figure 4:
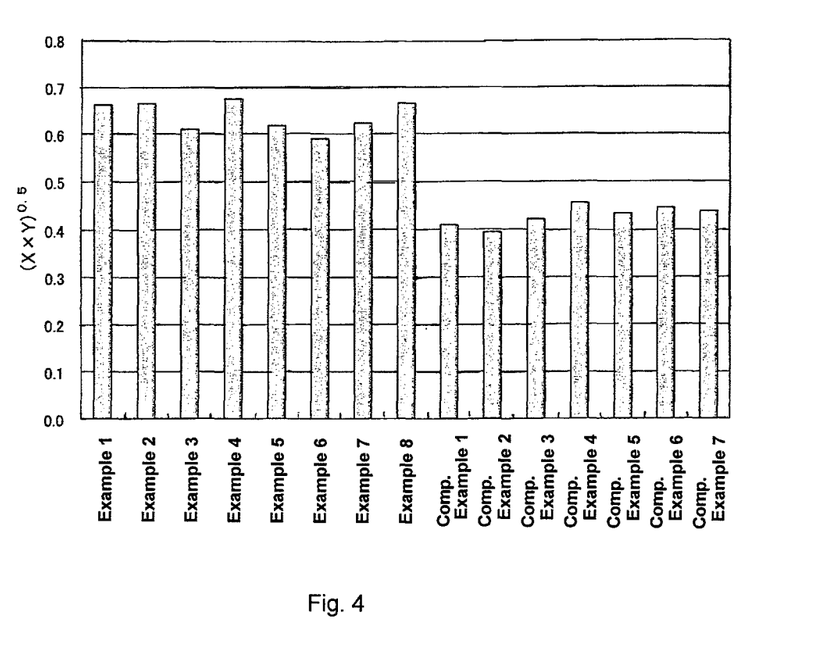
FIG. 4 is a graph showing the geometric mean $(X \times Y)^{0.5}$ of X and Y in Examples 1 to 8 and Comparative Examples 1 to 7.

Regarding the results of Examples 1 to 8 and Comparative Examples 1 to 7, the relationship between X (=ambient temperature filtration time $t_a$/cold filtration time $t_c$) and Y (=leukocyte removal performance in ambient temperature filtration $r_a$/leukocyte removal performance in cold filtration $r_c$) is summarized in FIG. 3. While X or Y was small in the comparative examples, X and Y were averagely large in the examples. FIG. 4 shows the geometric mean $(X \times Y)^{0.5}$ of X and Y. A significantly high geometric mean was obtained in the examples in comparison with the comparative examples.

Figure 5:
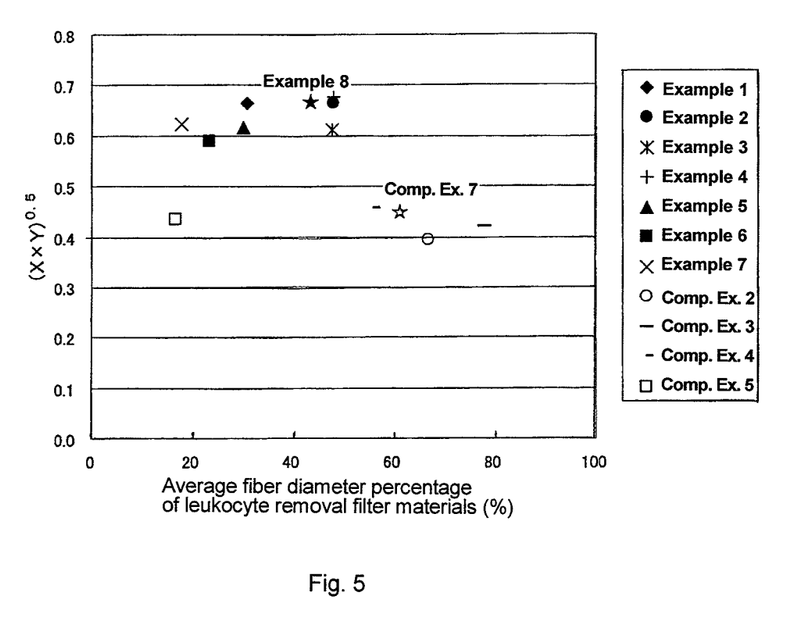
FIG. 5 is a graph showing the relationship between the average fiber diameter percentage of leukocyte removal filter materials and the geometric mean $(X \times Y)^{0.5}$ of X and Y in Examples 1 to 8 and Comparative Examples 2 to 5 and 7.

Regarding the results of Examples 1 to 8 and Comparative Examples 2 to 5 and 7, the relationship between the average fiber diameter percentage of the leukocyte removal filter materials (%) and the geometric mean $(X \times Y)^{0.5}$ of X and Y is shown in FIG. 5. The average fiber diameter percentage of the leukocyte removal filter materials shown in FIG. 5 is the percentage of the average fiber diameter of the filter material B with respect to that of the filter material A in the examples, and is the percentage of the average fiber diameter of the filter material having a smaller diameter with respect to that of the filter material having a larger diameter in two kinds of leukocyte removal filter materials in the comparative examples (since one leukocyte removal filter material was used in Comparative Examples 1 and 6, the percentage was not calculated). A significantly high geometric mean of X and Y was obtained in the examples in which the average fiber diameter percentage of the leukocyte removal filter materials was less than 50%. Comparative Example 5 exhibited an average fiber diameter percentage of 16.7%. However, since the fiber diameter of the filter material with a smaller diameter was too small, the geometric mean of X and Y was lower than those of the examples.

As described above, in the examples, a reduction in filtration time in cold filtration and an increase in leukocyte removal performance in ambient temperature filtration could be achieved at the same time by combining the filter material A and the filter material B having specific fiber diameters defined in the present invention and assigning the filter material A and the filter material B different functions. On the other hand, in the comparative examples, the filtration time in cold filtration was longer or the leukocyte removal performance in ambient temperature filtration was lower than those of the examples.

INDUSTRIAL APPLICABILITY

The leukocyte removal method according to the present invention can efficiently remove microaggregates and leukocytes or leukocytes and platelets from blood for transfusion in either ambient temperature filtration or cold filtration, and can be completed the filtration within a short period of time in comparison with the related art. Therefore, in particular the leukocyte removal method according to the present invention is extremely useful for removing leukocytes in a prestorage leukocyte reduction of a blood product in blood centers or the like.

TABLE 1

| Filter material | Average fiber diameter (μm) | Weight per unit area (g/m²) | Specific surface area (m²/g) | Amount of filter material (mg) | | | | | | | | | | | | |
|---|---|---|---|---|---|---|---|---|---|---|---|---|---|---|---|---|
| | | | | Example | | | | | | | Comparative Example | | | | | |
| | | | | 1 | 2 | 3 | 4 | 5 | 6 | 7 | 1 | 2 | 3 | 4 | 5 | 6 |
| $P_1$ | 12 | 30 | 0.24 | | | | | | | | 8.0 | | | | | |
| $P_2$ | 4.1 | 60 | 0.65 | | | | | | | | | | | | | 8.0 |
| $A_1$ | 3.9 | 60 | 0.7 | 8.0 | | | | | 8.0 | | | | | | | |
| $A_2$ | 2.5 | 60 | 0.8 | | 8.0 | | 16.0 | | | | | | | 8.0 | | |
| $A_3$ | 2.1 | 60 | 0.9 | | | 8.0 | | | | | | | | | | |
| $A_4$ | 3.0 | 60 | 0.75 | | | | | 8.0 | 8.0 | | | | | | 8.0 | |
| $C_1$ | 1.8 | 60 | 1.1 | | | | | 8.0 | | | | 8.0 | 8.0 | | | |
| $C_2$ | 1.4 | 40 | 1.3 | | | | | | | | | | 58.5 | 58.5 | | |
| $B_1$ | 1.2 | 40 | 1.5 | 58.5 | 58.5 | | 42.6 | | | | 58.5 | 58.5 | | | | |
| $B_2$ | 1.0 | 40 | 1.8 | | | 58.5 | | | | | | | | | | |
| $B_3$ | 0.9 | 40 | 2.0 | | | | | 58.5 | | | | | | | | 58.5 |
| $B_4$ | 0.7 | 40 | 2.5 | | | | | | 58.5 | 58.5 | | | | | | |
| D | 0.5 | 40 | 3.4 | | | | | | | | | | | | 58.5 | |
| Total amount of filter material (mg) | | | | 66.5 | 66.5 | 66.5 | 66.5 | 66.5 | 66.5 | 66.5 | 66.5 | 66.5 | 66.5 | 66.5 | 66.5 | 66.5 |
| Leukocyte removal filter material average fiber diameter percentage (%) | | | | $B_1/A_1$ 30.8 | $B_1/A_2$ 48.0 | $B_2/A_3$ 47.6 | $B_1/A_2$ 48.0 | $B_3/A_4$ 30.0 | $B_4/A_4$ 23.3 | $B_4/A_1$ 17.9 | — | $B_1/C_1$ 66.7 | $C_2/C_1$ 77.8 | $C_2/A_2$ 56.0 | $D_1/A_4$ 16.7 | — |
| Filter material A/B weight percentage (%) | | | | 13.6 | 13.6 | 13.6 | 37.5 | 13.6 | 13.6 | 13.6 | — | — | — | — | — | — |

TABLE 1-continued

| Filter material | | | Amount of filter material (mg) | | | | | | | | | | | | |
|---|---|---|---|---|---|---|---|---|---|---|---|---|---|---|---|
| | Average fiber diameter (μm) | Weight per unit area (g/m²) | Specific surface area (m²/g) | Example | | | | | | | Comparative Example | | | | |
| | | | | 1 | 2 | 3 | 4 | 5 | 6 | 7 | 1 | 2 | 3 | 4 | 5 | 6 |
| Ambient temperature filtration | $t_a$ = filtration time (min) | | | 24.0 | 27.6 | 30.8 | 18.2 | 33.5 | 40.9 | 38.8 | 32.4 | 33.6 | 29.3 | 13.7 | 56.4 | 47.3 |
| | $r_a$ = leukocyte removal performance | | | 2.8 | 3.0 | 3.2 | 2.6 | 3.6 | 3.8 | 3.8 | 3.3 | 3.4 | 2.4 | 1.7 | 4.2 | 3.5 |
| Cold filtration | $t_c$ = filtration time (min) | | | 37.2 | 46.8 | 60.0 | 29.6 | 67.3 | 93.0 | 81.3 | 141.5 | 162.8 | 116.3 | 33.9 | 250.5 | 184.7 |
| | $r_c$ = leukocyte removal performance | | | 4.1 | 4.0 | 4.4 | 3.5 | 4.7 | 4.8 | 4.7 | 4.5 | 4.5 | 3.4 | 3.3 | 5.0 | 4.5 |
| X = ambient temperature filtration time $t_a$/cold filtration time $t_c$ | | | | 0.65 | 0.59 | 0.51 | 0.61 | 0.50 | 0.44 | 0.48 | 0.23 | 0.21 | 0.25 | 0.40 | 0.23 | 0.26 |
| Y = ambient temperature leukocyte removal performance $r_a$/cold leukocyte removal performance $r_c$ | | | | 0.68 | 0.75 | 0.73 | 0.74 | 0.77 | 0.79 | 0.81 | 0.73 | 0.76 | 0.71 | 0.52 | 0.84 | 0.78 |
| $(X \times Y)^{0.5}$ | | | | 0.66 | 0.67 | 0.61 | 0.68 | 0.62 | 0.59 | 0.62 | 0.41 | 0.39 | 0.42 | 0.46 | 0.43 | 0.45 |

TABLE 2

| | | | | Amount of filter material (g) | |
|---|---|---|---|---|---|
| Filter material | Average fiber diameter (μm) | Weight per unit area (g/m²) | Specific surface area (m²/g) | Example 8 | Comparative Example 7 |
| $P_1$ | 12 | 30 | 0.24 | 0.67 | 0.67 |
| $A_2$ | 2.5 | 60 | 0.8 | 0.34 | |
| $C_1$ | 1.8 | 60 | 1.1 | 0.34 | 0.34 |
| $B_3$ | 1.1 | 40 | 1.6 | 4.93 | 5.60 |
| $C_1'$ | 1.8 | 60 | 1.1 | 0.34 | 0.34 |
| $A_2'$ | 2.5 | 60 | 0.8 | 0.34 | |
| $P_1'$ | 12 | 30 | 0.24 | 0.67 | 0.67 |
| Total amount of filter material (g) | | | | 7.62 | 7.62 |
| Leukocyte removal filter material | | | | $B_3/A_2$ | $B_3/C_1$ |
| average fiber diameter percentage (%) | | | | 44.0 | 61.1 |
| Filter material A/B weight percentage (%) | | | | 6.8 | — |
| Ambient temperature filtration | $t_a$ = filtration time (min) | | | 13 | 16 |
| | $r_a$ = leukocyte removal performance | | | 4.0 | 4.2 |
| Cold filtration | $t_c$ = filtration time (min) | | | 25 | 78 |
| | $r_c$ = leukocyte removal performance | | | 4.5 | 4.5 |
| X = ambient temperature filtration time $t_a$/cold filtration time $t_c$ | | | | 0.52 | 0.21 |
| Y = ambient temperature leukocyte removal performance $r_a$/cold leukocyte removal performance $r_c$ | | | | 0.89 | 0.93 |
| $(X \times Y)^{0.5}$ | | | | 0.68 | 0.44 |

The invention claimed is:

1. A leukocyte removal method comprising filtering blood containing leukocytes using a leukocyte removal filter including plural fibrous filter materials having different average fiber diameters to remove the leukocytes in the blood, in which the fibrous filter materials include at least a leukocyte removal filter material A having an average fiber diameter of not less than 2.1 μm to less than 4.0 μm and a leukocyte removal filter material B having an average fiber diameter of not less than 0.7 μm to less than 1.2 μm, the filter material B is disposed downstream of the filter material A, and the average fiber diameter of the leukocyte removal filter material B is more than 17.5% to less than 50% of the average fiber diameter of the filter material A,
wherein the leukocyte removal filter has a geometric mean $(X \times Y)^{0.5}$ of X and Y of not less than 0.5 to not more than 1 when a ratio ($t_a/t_c$) of a filtration time at a temperature of 20 to 24° C. ($t_a$) to a filtration time at a temperature of 1 to 6° C. ($t_c$) is assumed to be X, and a ratio ($r_a/r_c$) of a leukocyte removal filtration performance in the temperature of 20 to 24° C. ($r_a$) to a leukocyte removal filtration performance in the temperature of 1 to 6° C. ($r_c$) is assumed to be Y.

2. The leukocyte removal method according to claim 1, wherein the leukocyte removal filter includes a leukocyte removal filter material C having an average fiber diameter of more than 1.2 μm to less than 2.0 μm and disposed between the filter material A and the filter material B.

3. The leukocyte removal method according to claim 1, wherein the leukocyte removal filter includes the filter material A of which the weight in an effective filtration portion is not less than 2% to not more than 40% of the weight of the filter material B.

4. The leukocyte removal method according to claim 1, wherein the leukocyte removal filter further includes a filter material A' formed of the same material as the filter material A and disposed downstream of the filter material B, and the filter materials are symmetrically disposed with respect to a blood inlet side and a blood outlet side.

5. The leukocyte removal method according to claim 1, wherein the blood has previously been stored at 1 to 6° C. and is filtered at 1 to 6° C.

6. The leukocyte removal method according to claim 1, wherein the blood has been stored at 20 to 24° C. and is filtered at 20 to 24° C.

* * * * *